(12) United States Patent
Yang et al.

(10) Patent No.: US 11,733,146 B1
(45) Date of Patent: Aug. 22, 2023

(54) METHOD FOR DETERMINING COLUMN-HEMISPHERICAL PERMEATION RADIUS WITH TIME-VARYING PROPERTY OF POWER-LAW CEMENT GROUT AND TORTUOSITY OF ROCK AND SOIL MASS

(71) Applicant: Kunming University of Science and Technology, Kunming (CN)

(72) Inventors: Zhiquan Yang, Kunming (CN); Mao Chen, Kunming (CN); Yingyan Zhu, Kunming (CN); Yi Yang, Kunming (CN); Wentao Chen, Kunming (CN); Yuqing Liu, Kunming (CN); Muhammad Asif Khan, Kunming (CN); Bihua Zhang, Kunming (CN); Hanhua Xu, Kunming (CN); Tianbing Xiang, Kunming (CN); Jie Zhang, Kunming (CN)

(73) Assignee: KUNMING UNIVERSITY OF SCIENCE AND TECHNOLOGY, Kunming (CN)

( * ) Notice: Subject to any disclaimer, the term of this patent is extended or adjusted under 35 U.S.C. 154(b) by 0 days.

(21) Appl. No.: 18/072,319

(22) Filed: Nov. 30, 2022

(30) Foreign Application Priority Data

May 31, 2022 (CN) .......................... 202210608440.X

(51) Int. Cl.
*G01N 15/08* (2006.01)
*G01N 33/38* (2006.01)
*G01N 33/24* (2006.01)

(52) U.S. Cl.
CPC ....... *G01N 15/0893* (2013.01); *G01N 33/246* (2013.01); *G01N 33/383* (2013.01)

(58) Field of Classification Search
CPC .................................................. G01N 15/0893
See application file for complete search history.

(56) References Cited

U.S. PATENT DOCUMENTS

2021/0372954 A1* 12/2021 Elsayed ................... G01V 3/32

FOREIGN PATENT DOCUMENTS

CN 111853349 A * 10/2020 .............. F16L 1/036
CN 113297815 A 8/2021

OTHER PUBLICATIONS

CN-111853349-A—translate (Year: 2020).*
(Continued)

*Primary Examiner* — Kristina M Deherrera
*Assistant Examiner* — Fatemeh Esfandiari Nia
(74) *Attorney, Agent, or Firm* — Zhigang Ma

(57) ABSTRACT

A method for determining a column-hemispherical permeation radius with time-varying property of power-law cement grout and tortuosity of rock and soil mass is provided, including: acquiring a porosity φ of rock and soil mass and a corresponding permeation coefficient K by geotechnical tests, measuring a groundwater pressure $P_0$ at a grouting point and determining tortuosity ξ of rock and soil mass; acquiring an initial consistency coefficient $c_0$, a rheological index n and a time-varying property coefficient k of power-law cement grout with a designed water to cement ratio by rheological tests, and determining the viscosity of water $\mu_w$; acquiring grouting parameters, including a grouting pressure $P_1$, grouting time t, a number m of grouting holes of a side surface of a grouting pipe and a grouting hole radius r; and solving a column-hemispherical permeation grouting diffusion radius R considering coupling effect both the tortuosity of rock and soil mass and the time-varying property of power-law cement grout.

7 Claims, 5 Drawing Sheets

(56) References Cited

OTHER PUBLICATIONS

Wang, Xuesong, et al. "Theoretical Research on Sand Penetration Grouting Based on Cylindrical Diffusion Model of Tortuous Tubes." Water 14.7 (2022): 1028 (Year: 2022).*

Yang Xiu-zhu, Lei Jin-shan, Xia Li-nong, Wang Xing-hua, "Study on grouting diffusion radius of exponential fluids", Rock and Soil Mechanics, Nov. 2005, pp. 1803-1806, vol. 26, No. 11.

Yang Zhiquan, Niu Xiangdong, Hou Kepeng, Guo Yanhui, Liang Wei, Zhou Zonghong, "Column penetration grouting mechanism researches based on Power-law fluid", Journal of Harbin Institute of Technology, Mar. 2016, pp. 178-183, vol. 48, No. 3.

Yang Zhiquan, Hou Kepeng, Cheng Yong, Yang Bajiu, "Study of Column-Hemispherical Penetration Grouting Mechanism Based on Power-Law Fluid", Chinese Journal of Rock Mechanics and Engineering, Aug. 2014, pp. 3840-3846, vol. 33, supp.2.

Ye Fei, Chen Zhi, Jia Tao, Mao Yan-fei, Mao Jia-hua, "Penetration diffusion model of exponential fluid for backfill grouting through segments of shield tunnel", Chinese Journal of Geotechnical Engineering, May 2016, pp. 890-897, vol. 38, No. 5.

Zhang Cong, Liang Jin-wei, Yang Jun-sheng, Zhang Gui-jin, Xie Yi-peng, Ye Xin-tian, "Diffusion mechanism of pulsating seepage grouting slurry with power-law fluid considering interval distribution", Chinese Journal of Geotechnical Engineering, Nov. 2018, pp. 2120-2128, vol. 40, No. 11.

Yang Jian, Tan Junkun, Liu Ritong, Zhang Xibao, Peng Zumin, "Study on Cylindrical Diffusion of Grouting Behind Segment Wall Considering Time-Varying Consistency of Exponential Slurry", Railway Engineering, Nov. 2020, vol. 60, No. 11.

Zhang Kun, "Study on the mechanism of porous medium infiltration grouting considering tortuosity", Kunming University of Science and Technology, 2019, pp. 89.

CNIPA, Notification of a First Office Action for CN202210608440.X, dated Jul. 18, 2022.

Chengdu University of Technology, Kunming University of Science Technology (Applicants), Reply to Notification of a First Office Action for CN202210608440.X, w/ replacement claims, dated Jul. 18, 2022.

Chengdu University of Technology, Kunming University of Science Technology (Applicants), Supplemental Reply to Notification of a First Office Action for CN202210608440.X, w/ (allowed)replacement claims, dated Jul. 26, 2022.

CNIPA, Notification to grant patent right for invention in CN202210608440.X, dated Aug. 2, 2022.

* cited by examiner

```
┌─────────────────────────────────────────────────────────────┐
│ Acquiring porosity of rock and soil mass and corresponding  │
│ permeation coefficient by rock and soil mass tests, measuring │
│ to acquire the groundwater pressure at a grouting point and  │
│ determining tortuosity of rock and soil mass.                │
└─────────────────────────────────────────────────────────────┘
                              │
                              ▼
┌─────────────────────────────────────────────────────────────┐
│ Obtaining initial consistency coefficient, rheological index │
│ and time-varying property coefficient of power-law cement    │
│ grout with designed water to cement ratio by rheological     │
│ tests, and the viscosity of water is determined.             │
└─────────────────────────────────────────────────────────────┘
                              │
                              ▼
┌─────────────────────────────────────────────────────────────┐
│ Acquiring grouting parameters, the grouting parameters       │
│ including grouting pressure, grouting time, the number of    │
│ side surface grouting holes of grouting pipe and grouting    │
│ hole radius.                                                 │
└─────────────────────────────────────────────────────────────┘
                              │
                              ▼
┌─────────────────────────────────────────────────────────────┐
│ Obtaining the diffusion radius of column-hemispherical       │
│ permeation grouting.                                         │
└─────────────────────────────────────────────────────────────┘
```

FIG. 1

METHOD FOR DETERMINING COLUMN-HEMISPHERICAL PERMEATION RADIUS WITH TIME-VARYING PROPERTY OF POWER-LAW CEMENT GROUT AND TORTUOSITY OF ROCK AND SOIL MASS

TECHNICAL FIELD

The disclosure relates to the technical field of environmental protection and ecological restoration, in particular to a method for determining a column-hemispherical permeation radius with time-varying property of power-law cement grout and tortuosity of rock and soil mass.

BACKGROUND

Permeation grouting of grouting fluid in the rock and soil mass can show three diffusion forms: spherical, cylindrical and column-hemispherical. According to different rheological constitutive equations, the grouting fluid can be divided into three types: Newtonian fluid, Bingham fluid and Power-law fluid. Pores of the rock and soil mass are distributed tortuously, so that permeation and diffusion channel of the fluid therein is not a straight path, but has a typical tortuous effect. At the same time, the rheological parameters of cement grout are not constant, but will change with time, which has a typical time-varying property effect. If the tortuous effect (i.e., tortuosity) of the rock and soil mass and the time-varying property of the cement grout are not considered, obviously, it is seriously inconsistent with an actual permeation and diffusion condition of the cement grout in the rock and soil mass, and the permeation and diffusion effect of cement grout in the rock and soil mass cannot be truly reflected. However, permeation grouting mechanism in the existing arts has not considered the influence of coupling effect both tortuosity of the rock and soil mass and time-varying property of the cement grout on the permeation and diffusion effect, so that diffusion parameters calculated by the existing arts are far larger than actual values in practical grouting engineering, which is difficult to meet the needs of engineering practice.

At present, some scholars have done some researches on the permeation and diffusion law of the power-law fluid in the rock and soil mass. In the aspect of permeation and diffusion mechanism without considering the time-varying property of rheological parameters of the power-law fluid, for example, YANG Xiuzhu et al. deduced the formula of permeation grouting diffusion radius of the power-law fluid diffused spherically in the rock and soil mass (YANG Xiuzhu et al., "STUDY ON GROUTING DIFFUSION RADIUS OF EXPONENTIAL FLUIDS", Rock and Soil Mechanics, November, 2005, pages 1803-1806, Vol. 26, No. 11.). On the basis of YANG Xiuzhu et al., YANG Zhiquan et al. discussed the permeation grouting mechanism of the power-law fluid diffused in the rock and soil mass with the cylindrical and column-hemispherical forms respectively (YANG Zhiquan et al., "COLUMN PENETRATION GROUTING MECHANISM RESEARCHES BASED ON POWER-LAW FLUID" JOURNAL OF HARBIN INSTITUTE OF TECHNOLOGY, March 2016, pages 178-183, Vol. 48, No. 3, and "STUDY OF COLUMN-HEMISPHERICAL PENETRATION GROUTING MECHANISM BASED ON POWER-LAW FLUID", Chinese Journal of Rock Mechanics and Engineering, August 2014, pages 3840-3846, Vol. 33, supp. 2.). YE Fei et al. published "PENETRATION DIFFUSION MODEL OF EXPONENTIAL FLUID FOR BACKFILL GROUTING THROUGH SEGMENTS OF SHIELD TUNNEL" on Chinese Journal of Geotechnical Engineering, May 2016, pages 890-897, Vol. 38, No. 5. ZHANG Cong et al. published "DIFFUSION MECHANISM OF PULSATING SEEPAGE GROUTING SLURRY WITH POWER-LAW FLUID CONSIDERING INTERVAL DISTRIBUTION" on Chinese Journal of Geotechnical Engineering, November 2018, pages 2120-2128, Vol. 40, No. 11. In the aspect of the permeation and diffusion law considering the time-varying property of the rheological parameters of the power-law fluid, YANG Zhiquan et al. researched the permeation grouting mechanism of the power-law cement grout diffused spherically and cylindrically in the rock and soil mass considering the time-varying property of rheological parameters, and YANG Jian et al. analyzed the post-grouting cylindrical diffusion law of a tunnel segment wall of the power-law cement grout considering a consistency time-varying effect (YANG Jian et al., "Study on Cylindrical Diffusion of Grouting Behind Segment Wall Considering Time-Varying Consistency of Exponential Slurry", Railway Engineering, November 2020, Vol. 60, No. 11.). In the aspect of considering the influence of the tortuosity of the rock and soil mass on permeation and diffusion, ZHANG Kun and YANG Zhiquan respectively researched the spherical and cylindrical permeation grouting mechanism of the power-law fluid considering the tortuosity of the rock and soil mass (ZHANG Kun, "Study on the mechanism of porous medium infiltration grouting considering tortuosity", Kunming University of Science and Technology, 2019, pages 89.).

Another example is the Chinese patent with a patent publication number of CN113297815A and entitled "BINGHAM TYPE CEMENT GROUT PERMEATION GROUTING DIFFUSION RADIUS CALCULATION METHOD CONSIDERING POROUS LOOSE MEDIUM TORTUOSITY", which acquires yield stress and plastic viscosity in a Bingham fluid constitutive equation through a Bingham fluid rheological curve, and acquires Bingham cement grout rheological equations with different water to cement ratios; according to the tortuosity of the Bingham cement grout in the rock and soil mass flow path and the Bingham cement grout rheological equation, a permeation motion equation of the Bingham fluid considering the tortuosity of the porous loose medium is derived; according to grouting initial conditions and boundary conditions, the calculation formula for the permeation grouting diffusion radius of the Bingham cement grout considering the influence of the tortuosity of the porous loose medium is derived. This technology only considers the influence of the tortuosity of the porous loose medium on the permeation grouting diffusion radius of the Bingham cement grout, but does not consider time-varying property of cement grout. At the same time, the cement grout can be divided into three types: Newtonian fluid, Bingham fluid and Power-law fluid according to different rheological constitutive equations, cement grout of different fluid types has different permeation grouting mechanisms in the rock and soil mass, and such technology takes the Bingham cement grout as the research object, but the disclosure explores the power-law cement grout, and thus they have different methods to determine the permeation grouting diffusion radius.

According to the engineering practice and theoretical research, it is shown that the time-varying property of power-law fluid and the tortuosity of rock and soil mass have very important influences on the permeation and diffusion process and the grouting effect; however, from the above research results, it can be seen that the current permeation grouting mechanisms do not considered the influence of the coupling effect both the tortuosity of rock and soil mass and the time-varying property of the power-law fluid on the permeation and diffusion process and the grouting effect yet, and even the related results of column-hemispherical permeation grouting mechanisms of the power-law fluid only considering respective influences of the time-varying property of the power-law fluid and the tortuosity of rock and soil mass have not been published. It can be seen that the current permeation grouting theories are difficult to meet the needs of grouting engineering practice. Therefore, the column-hemispherical permeation grouting diffusion radius considering the coupling effect both the tortuosity of rock and soil mass and the time-varying property of power-law cement grout cannot be reasonably and effectively determined.

Therefore, it is urgent to provide a method for determining the column-hemispherical permeation radius with the time-varying property of the power-law cement grout and the tortuosity of the rock and soil mass, which considers the coupling effect both the time-varying property of the power-law cement grout and the tortuosity of the rock and soil mass, and more accords with the grouting engineering practice.

SUMMARY

In view of the above problems, the objective of the disclosure is to provide a method for determining a column-hemispherical permeation radius with time-varying property of power-law cement grout and tortuosity of rock and soil mass.

The method for determining the column-hemispherical permeation radius with the time-varying property of power-law cement grout and the tortuosity of rock and soil mass, which includes the following steps:

acquiring a porosity $\phi$ of rock and soil mass and its corresponding permeation coefficient K by the rock and soil mass tests, and measuring a groundwater pressure $P_0$ at a grouting point, and determining the tortuosity $\xi$ of the rock and soil mass;

acquiring an initial consistency coefficient $c_0$, a rheological index n and a time-varying property coefficient k of the power-law cement grout with a designed water to cement ratio by rheological tests, and determining a viscosity of the water $\mu_w$;

acquiring grouting parameters, which include a grouting pressure $P_1$, grouting time t, a number m of grouting holes of a side surface of a grouting pipe and a grouting hole radius r;

solving a column-hemispherical permeation grouting diffusion radius R as the column-hemispherical permeation radius considering a coupling effect both the tortuosity of the rock and soil mass and the time-varying property of power-law cement grout by using a Formula (1), which is expressed as:

$$\Delta p = p_1 - p_0 = \frac{2^{1+n} c_0 e^{kt} \sqrt{\xi}}{1-2n} \left(\frac{m+1}{4m+5}\right)^n \left(\frac{3n+1}{tn}\right)^n \left(\frac{\phi \rho_w g}{8\mu_w K}\right)^{\frac{n+1}{2}} (R^{1-2n} - r^{1-2n}) R^{3n} \tag{1}$$

where $\rho_\omega$ represents a water density; g is a gravitational acceleration; e represents a base of a natural logarithm.

The expression of the porosity $\phi$ of the rock and soil mass is:

$$\phi = 1 - \frac{\rho}{G_S \rho_W^{4° C.}(1+\omega)} \tag{2}$$

where $\rho_W^{4° C.}$ is a density of pure distilled water at 4° C.; $\rho$ represents a density of the rock and soil mass; $\omega$ represents a mass water content of the rock and soil mass; $G_s$ represents a specific gravity of the rock and soil mass.

In an embodiment, the density $\rho$ of the rock and soil mass is acquired by one of an irrigation method, a sand filling method, and a cutting ring method.

In an embodiment, the mass water content $\omega$ of the rock and soil mass is measured by a drying method.

In an embodiment, the specific gravity $G_s$ of the rock and soil mass is measured by combining a pycnometer method and a siphon cylinder method.

In an embodiment, the permeation coefficient K is acquired by field water injection tests.

The expression of the tortuosity $\xi$ of the rock and soil mass is:

$$\xi = \left(\frac{L_e}{L}\right)^2 \tag{3}$$

where $L_e$ represents an actual flow path length of the cement grout into the rock and soil mass; L is a linear length corresponding to the actual flow path of the cement grout into the rock and soil mass.

In an embodiment, the acquiring an initial consistency coefficient $c_0$, a rheological index n and a time-varying property coefficient k of the power-law cement grout with a designed water to cement ratio by rheological tests includes the following steps:

performing the rheological tests of the power-law cement grout with the designed water to cement ratio at different times by using a rotary viscometer or a capillary viscometer;

establishing a shear velocity-shear stress coordinate system, and acquiring rheological curves corresponding to the rheological tests;

obtaining a rheological equation corresponding to the rheological curve in accordance with a power-law fluid rheology equation, and then acquiring a consistency coefficient c and the rheological index n correspondingly; and obtaining the initial consistency coefficient $c_0$, the rheological index n and the time-varying property coefficient k of the power-law cement grout with the designed water to cement ratio by analyzing change relationships between the consistency coefficient c, the rheological index n and time T.

Compared with the existing technologies, the disclosure has the following beneficial effects.

(1) Aiming at the shortcomings of the current permeation grouting theories and the technical problems in actual grouting engineering, the disclosure takes the power-law cement grout (the cement grout with water to cement ratio of 0.50-0.75) widely used in the grouting engineering practice at home and abroad as a research object, and provides the method for determining the column-hemispherical permeation radius with the time-varying property of the power-law cement grout and the tortuosity of the rock and soil mass considering the coupling effect both the time-varying property of the power-law cement grout and the tortuosity of the rock and soil mass, which can better reflect the permeation grouting diffusion law of the power-law cement grout into the rock and soil mass, and the acquired diffusion radius more accords with the grouting engineering practice, which can guide application of the grouting practical engineering and improve the technical level of rock and soil mass reinforcement by the permeation grouting.

(2) According to the grouting practice engineering, under the condition that an actual diffusion radius of the power-law cement grout in the rock and soil mass is known, the disclosure can also acquire a required relatively precise grouting pressure by back calculation according to the method for determining the column-hemispherical permeation radius with the time-varying property of the power-law cement grout and the tortuosity of the rock and soil mass considering the coupling effect both the time-varying property of the power-law cement grout and the tortuosity of the rock and soil mass, so as to avoid the waste of engineering materials and save engineering costs.

In summary, the disclosure has the advantages of simple logic, accuracy and reliability and the like, and has very high practical value and popularization value in the field of environmental protection and ecological restoration technologies.

BRIEF DESCRIPTION OF DRAWINGS

In order to more clearly explain the technical schemes of the embodiment of the disclosure, the following briefly introduces the accompanying drawings required for describing the embodiments. It should be understood that the follow accompanying drawings merely show some embodiments of the disclosure and thus should not be considered to limit the protective scope, for technicians in this field, other relevant drawings can also be obtained based on these drawings without paying for creative work.

FIG. 1 is a logic flowchart of the disclosure.

In the above drawings, the names of parts corresponding to reference signs are as follows:

1—grouting pipe; 2—side surface grouting hole; 3—bottom grouting hole; 4—rock and soil mass; 5—pore.

DETAILED DESCRIPTION OF EMBODIMENTS

The disclosure will be described in further detail in combination with the accompanying drawings and embodiments, to present the objectives, technical solutions, and advantages of the present application clearly. The embodiments of the disclosure include but not limited to the following embodiments. Based on the embodiments in this application, all other embodiments obtained by ordinary technicians in this field without making creative labor are covered by the protection in this application.

Embodiment 1

Figure 2:
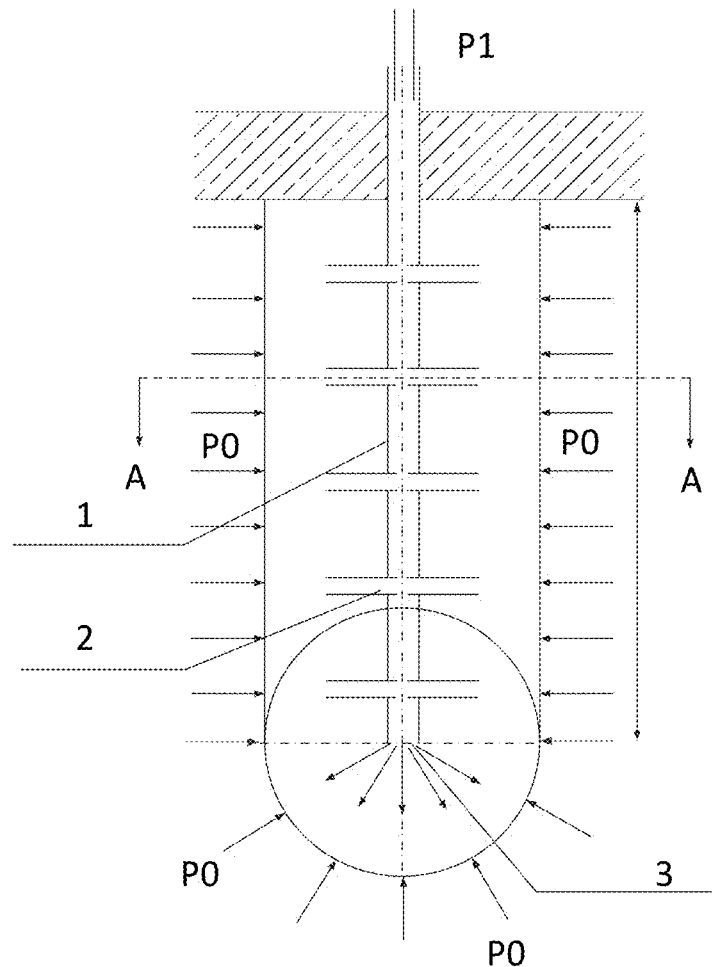
FIG. 2 is a diagram of column-hemispherical permeation grouting diffusion form of power-law cement grout into rock and soil mass in the disclosure.
Figure 3:
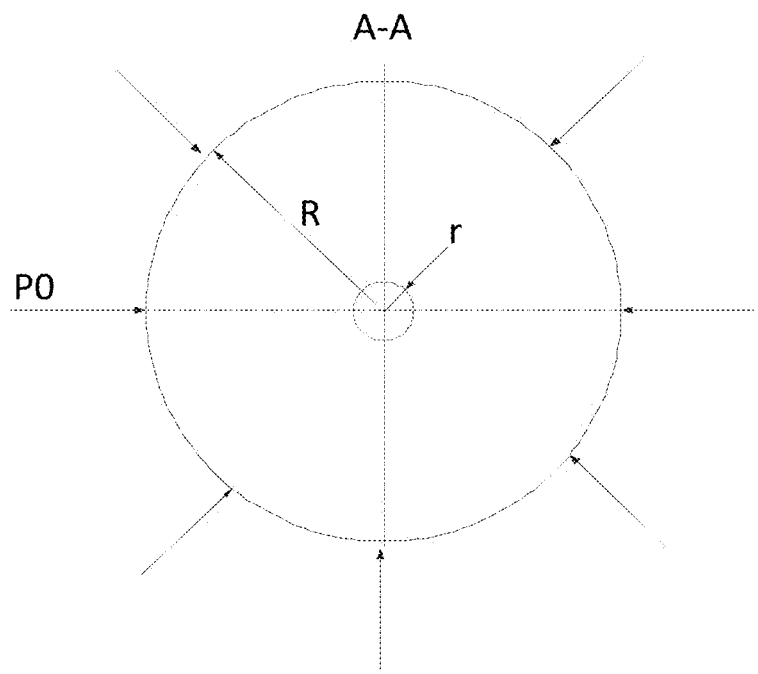
FIG. 3 is A-A view of FIG. 2.

As shown in FIG. 1 to FIG. 7, the present embodiment provides a method for determining column-hemispherical permeation radius with the time-varying property of power-law cement grout and the tortuosity of the rock and soil mass, which considers the coupling effect both the time-varying property of power-law cement grout and the tortuosity of rock and soil mass. As shown in FIG. 2 to FIG. 3, the grouting enters side surface grouting hole 2 and bottom grouting hole 3 from the grouting pipe 1, and the groundwater pressure at the external grouting point of the grouting area is $p_0$.

Figure 4:
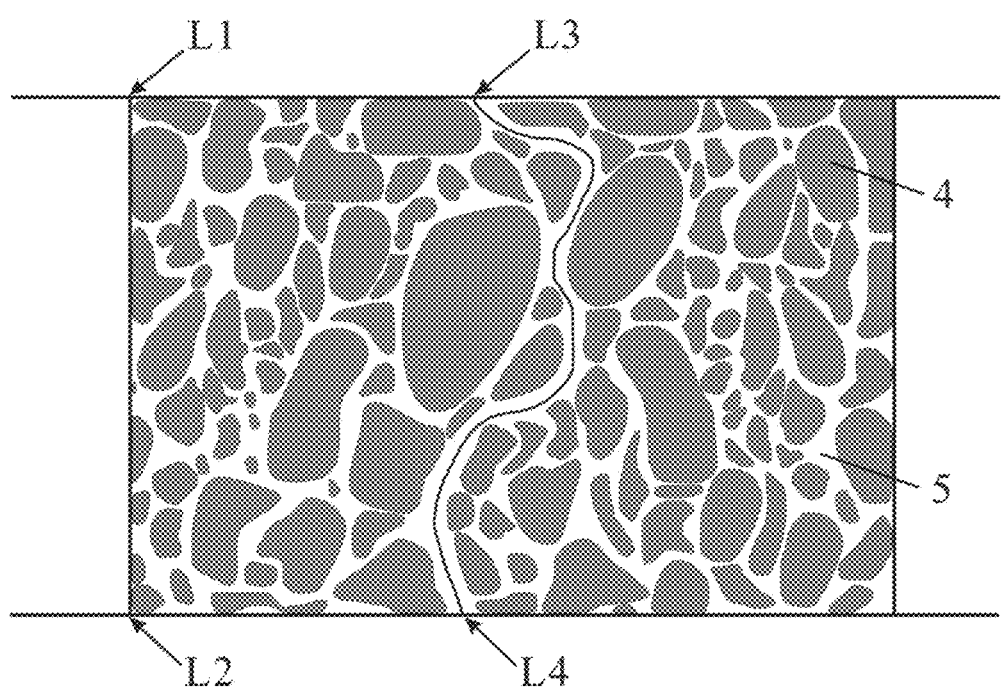
FIG. 4 is a schematic diagram of actual permeation and diffusion flow path of the power-law cement grout into the rock and soil mass in the disclosure.

The specific steps are as follows:

1) The porosity $\phi$ is equal to 48.97%, the permeation coefficient K is equal to 0.0118 m/s and the groundwater pressure at the grouting point $p_0$ is equal to 0 Pa by using geotechnical tests. Meanwhile, according to existing research results, the tortuosity $\xi$ of the rock and soil mass is selected to be equal to 2.25, as shown in FIG. 4, in the rock and soil mass 4 and pores 5, the actual permeation and diffusion flow path of the cement grout into the rock and soil mass 4 (the path L1-L2 is the theoretical flow path of the fluid, and the path L3-L4 is the actual flow path of the fluid).

The porosity $\phi$ of the rock and soil mass is calculated by the following formula, where:

$$\phi = 1 - \frac{\rho}{G_S \rho_W^{4°\,C.}(1+\omega)}$$

where $\rho_W^{4°\,C.}$ is 1000 kg/m³; and by the rock and soil mass tests, it is measured for the rock and soil mass that the density $\rho$ is equal to 1355 kg/m³, the mass water content $\omega$ is equal to 0.20%, and the specific gravity is equal to 2.65.

2) The initial consistency coefficient $c_0=10.4426$ Pa·s$^n$, rheological index n=0.1406, time-varying property coefficient k=0.0011 of power-law cement grout with water to cement ratio of 0.50 and the viscosity of water $\mu_w=1.31\times10^{-3}$ Pa·s are obtained by rheological tests.

Figure 5:
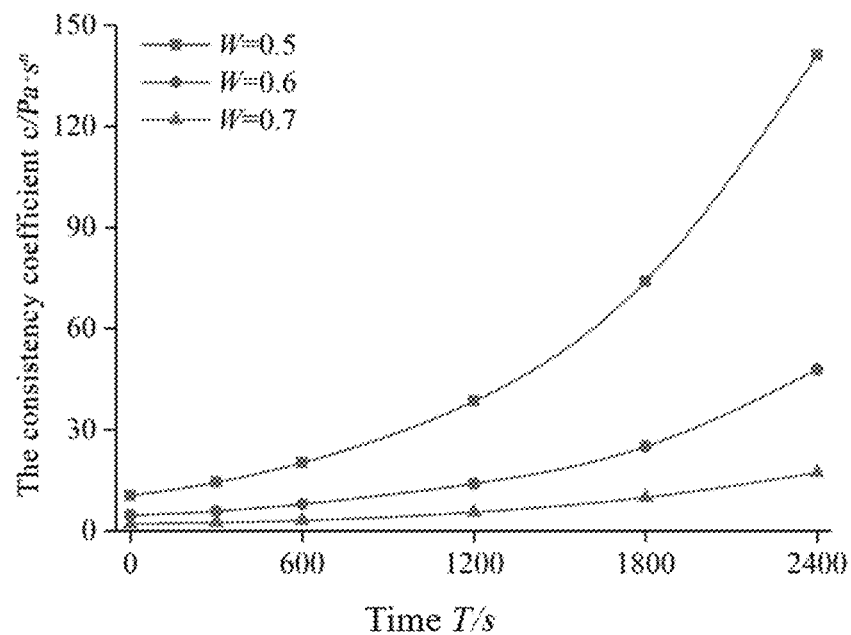
FIG. 5 is the variation curve of the consistency coefficient of water to cement ratio 0.50, 0.60 and 0.70 power-law cement grout with time in the disclosure.
Figure 6:
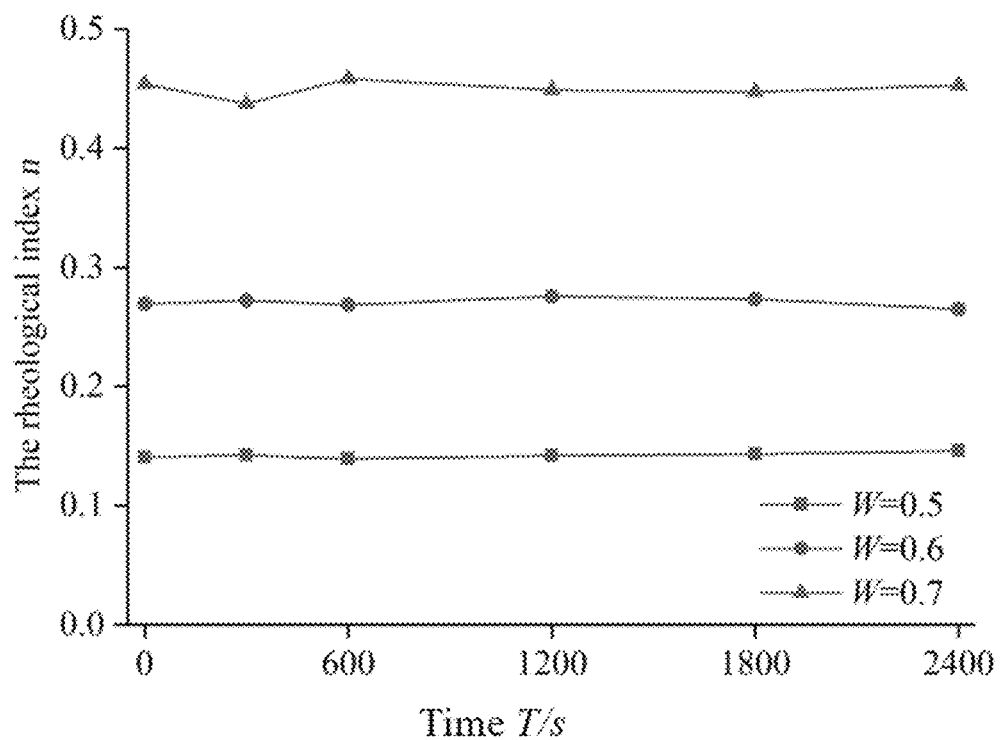
FIG. 6 is a curve diagram of change law of rheological index of the power-law cement grout with water to cement ratio of 0.50, 0.60 and 0.70 with time in the disclosure.
Figure 7:
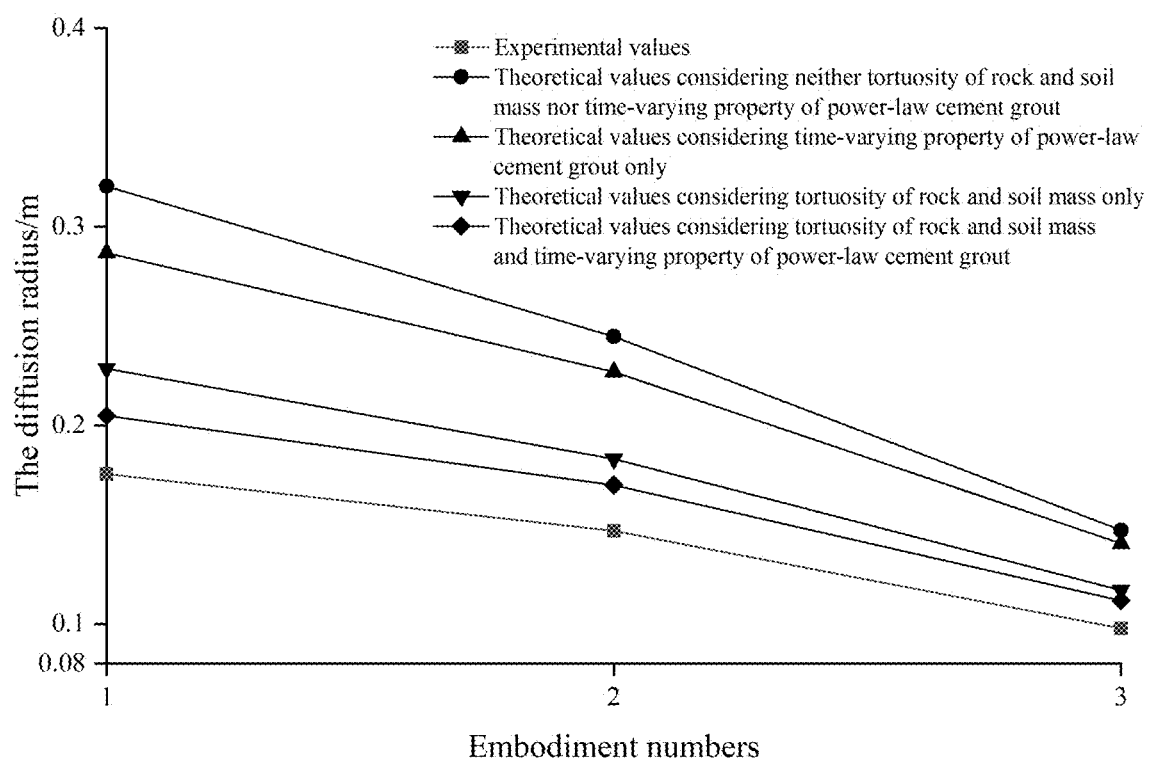
FIG. 7 is a comparison diagram between theoretical values and experimental values of the permeation and diffusion radius of the power-law cement grout with water to cement ratio of 0.50, 0.60 and 0.70 into the rock and soil mass.

In the present embodiment, the change laws between the consistency coefficient c and the rheological index n of the power-law cement grout with water to cement ratio of 0.50 and time are shown in FIG. 5 to FIG. 6 respectively. Through analysis, it can be known that the consistency coefficient has a power-exponential change relationship with time, and has time-varying property; however, the rheological index changes little with time, which can be regarded as time-invariant. From this research, the initial consistency coefficient, the rheological index and the time-varying property coefficient of the power-law cement grout with water to cement ratio of 0.50 can be acquired.

3) According to the actual situation, it is designed that grouting pressure $p_1$ is equal to 100000 Pa, grouting time t is equal to 120 s, the number m of side surface grouting holes of grouting pipe is equal to 3 and its radius r is equal to $7.5\times10^{-3}$ m;

4) The column-hemispherical permeation grouting diffusion radius R considering the coupling effect both tortuosity of rock and soil mass and time-varying property of power-law cement grout is acquired by using the following formula, and the expression formula is:

$$\Delta p =$$

$$p_1 - p_0 = \frac{2^{1+n} c_0 e^{kt} \sqrt{\xi}}{1-2n} \left(\frac{m+1}{4m+5}\right)^n \left(\frac{3n+1}{tn}\right)^n \left(\frac{\phi \rho_w g}{8\mu_w K}\right)^{\frac{n+1}{2}} (R^{1-2n} - r^{1-2n}) R^{3n}$$

Where formula, $p_1$ is the grouting pressure (Pa); $p_0$ is the groundwater pressure at the grouting point (Pa); $c_0$, n and k are the initial consistency coefficient (Pa·s$^n$), the rheological index (dimensionless number) and the time-varying property coefficient (dimensionless number) of the power-law cement grout respectively; t is the grouting time (s); $\xi$, $\phi$ and K are the tortuosity (dimensionless number), the porosity (dimensionless number) and the permeation coefficient (m/s) of the rock and soil mass respectively; m is the number of side surface grouting holes of grouting pipe (dimensionless number); $\rho_w$ takes 1000 kg/m$^3$; g takes 9.8 m/s$^2$; $\mu_w$ is the viscosity of water (Pa·s); R is the diffusion radius (m) of the power-law cement grout in the rock and soil mass; r is the radius (m) of the grouting hole.

Through analysis, it is determined that the theoretical value of the diffusion radius acquired by the method for determining the column-hemispherical permeation radius with the time-varying property of the power-law cement grout and the tortuosity of the rock and soil mass considering the coupling effect both the time-varying property of the power-law cement grout and the tortuosity of the rock and soil mass in the present embodiment is 0.2049 m. However, the theoretical values of the diffusion radius acquired by using the methods for calculating the column-hemispherical permeation grouting diffusion radius considering neither the tortuosity of the rock and soil mass nor the time-varying property of the power-law cement grout, only considering the tortuosity of the rock and soil mass and only considering the time-varying property of the power-law cement grout are 0.3204 m, 0.2285 m and 0.2869 m respectively, and the experimental value carried out according to the implementation is 0.1754 m. At the same time, by analyzing FIG. 7, it can be seen that the theoretical value of the diffusion radius acquired by the method for determining the column-hemispherical permeation radius with the time-varying property of the power-law cement grout and the tortuosity of the rock and soil mass considering the coupling effect both the time-varying property of the power-law cement grout and the tortuosity of the rock and soil mass in the present embodiment is closer to the experimental value than the theoretical values of the diffusion radius respectively acquired by using the methods for calculating the column-hemispherical permeation grouting diffusion radius considering neither the tortuosity of the rock and soil mass nor the time-varying property of the power-law cement grout, only considering the tortuosity of the rock and soil mass and only considering the time-varying property of the power-law cement grout.

Embodiment 2

The present embodiment provides a method for determining column-hemispherical permeation radius with the time-varying property of power-law cement grout and tortuosity of the rock and soil mass, and the specific steps are as follows:

1) By using the rock and soil mass tests, it can be acquired for the rock and soil mass that the porosity $\phi$ is equal to 44.19%, the permeation coefficient K is equal to 0.0083 m/s and the groundwater pressure $p_0$ at the grouting point is equal to 0 Pa. Meanwhile, according to the existing research results, the tortuosity $\xi$ of the rock and soil mass is selected to be equal to 2.25;

The porosity $\phi$ parameters of the rock and soil mass are as follows: by the rock and soil mass tests, it is measured for the rock and soil mass that the density $\rho$ is equal to 1482 kg/m$^3$, the mass water content U) is equal to 0.20%, and the specific gravity is equal to 2.65.

2) By conducting the rheological tests, it can be acquired for the power-law cement grout with water to cement ratio of 0.60 that the initial consistency coefficient $c_0$ is equal to 4.6156 Pa·s$^n$, the rheological index n is equal to 0.2692, the time-varying property coefficient k is equal to 0.0010 and the viscosity of water $\mu_w$ is equal to 1.31×10$^{-3}$ Pa·s;

In the present embodiment, the change laws between the consistency coefficient c and the rheological index n of the power-law cement grout with water to cement ratio of 0.60 and time are shown in FIG. 5 to FIG. 6 respectively. Through analysis of these two figures, it can be known that the consistency coefficient has a power-exponential change relationship with time, and has time-varying property; however, the rheological index changes little with time, which can be regarded as time-invariant. From this research, the initial consistency coefficient, the rheological index and the time-varying property coefficient of the power-law cement grout with water to cement ratio of 0.60 can be acquired.

3) According to the actual situation, it is designed that grouting pressure $p_1$ is equal to 80000 Pa, grouting time t is equal to 105 s, the number of side surface grouting holes of grouting pipe is equal to 3 and its radius r is equal to 7.5×10$^{-3}$ m;

4) The column-hemispherical permeation grouting diffusion radius R considering the coupling effect both the tortuosity of rock and soil mass and the time-varying property of power-law cement grout is solved.

Through analysis, it is determined that the theoretical value of the diffusion radius acquired by the method for determining the column-hemispherical permeation radius with the time-varying property of the power-law cement grout and the tortuosity of the rock and soil mass considering the coupling effect both the time-varying property of the power-law cement grout and the tortuosity of the rock and soil mass in the present embodiment is 0.1699 m. However, the theoretical values of the diffusion radius acquired by using the methods for calculating the column-hemispherical permeation grouting diffusion radius considering neither the tortuosity of the rock and soil mass nor the time-varying property of the power-law cement grout, only considering the tortuosity of the rock and soil mass and only considering the time-varying property of the power-law cement grout are 0.2447 m, 0.1830 m and 0.2269 m respectively, and the experimental value carried out according to the implementation is 0.1469 m. At the same time, by analyzing FIG. 7, it can be seen that the theoretical value of the diffusion radius acquired by the method for determining the column-hemispherical permeation radius with the time-varying property of the power-law cement grout and the tortuosity of the rock and soil mass considering the coupling effect both the time-varying property of the power-law cement grout and the tortuosity of the rock and soil mass in the present embodiment is closer to the experimental value than the theoretical values of the diffusion radius respectively acquired by using the methods for calculating the column-hemispherical permeation grouting diffusion radius considering neither the tortuosity of the rock and soil mass nor the time-varying property of the power-law cement grout, only considering the tortuosity of the rock and soil mass and only considering the time-varying property of the power-law cement grout.

Embodiment 3

The present embodiment provides a method for determining column-hemispherical permeation radius with the time-varying property of power-law cement grout and the tortuosity of the rock and soil mass, and the specific steps are as follows:

1) By using the rock and soil mass tests, it can be acquired for the rock and soil mass that the porosity $\phi$ is equal to 40.31%, the permeation coefficient K is equal to 0.0055 m/s and the groundwater pressure $p_0$ at the grouting point is equal to 0 Pa. Meanwhile, according to the existing research results, the tortuosity $\xi$ of the rock and soil mass is selected to be equal to 2.25;

The porosity $\phi$ parameters of the rock and soil mass are as follows: by the rock and soil mass tests, it is measured for the rock and soil mass that the density $\rho$ is equal to 1585 kg/m$^3$, the mass water content $\omega$ is equal to 0.20%, and the specific gravity is equal to 2.65.

2) By the rheological tests, it can be acquired for the power-law cement grout with water to cement ratio of 0.70 that initial consistency coefficient $c_0$ is equal to 1.9321 Pa·s$^n$, rheological index n is equal to 0.4537, time-varying property coefficient k is equal to 0.0009 and the viscosity of water is equal to $1.31 \times 10^{-3}$ Pa·s;

In the present embodiment, the change laws between the consistency coefficient c and the rheological index n of the power-law cement grout with the water to cement ratio of 0.70 and time are shown in FIG. 5 to FIG. 6 respectively. Through analysis of these two figures, it can be known that the consistency coefficient has a power-exponential change relationship with time, and has time-varying property; however, the rheological index changes little with time, which can be regarded as time-invariant. From this research, the initial consistency coefficient, the rheological index and the time-varying property coefficient of the power-law cement grout with the water to cement ratio of 0.70 can be acquired.

3) According to the actual situation, it is designed that the grouting pressure $p_1$ is equal to 60000 Pa, grouting time t is equal to 90 s, the number m of side surface grouting holes of grouting pipe is equal to 3 and its radius r is equal to $7.5 \times 10^{-3}$ m;

4) The column-hemispherical permeation grouting diffusion radius R considering the coupling effect both the tortuosity of rock and soil mass and the time-varying property of power-law cement grout is solved.

Through analysis, it is determined that the theoretical value of the diffusion radius acquired by the method for determining the column-hemispherical permeation radius with the time-varying property of the power-law cement grout and the tortuosity of the rock and soil mass considering the coupling effect both the time-varying property of the power-law cement grout and the tortuosity of the rock and soil mass in the present embodiment is 0.1117 m. However, the theoretical values of the diffusion radius acquired by using the methods for calculating the column-hemispherical permeation grouting diffusion radius considering neither the tortuosity of the rock and soil mass nor the time-varying property of the power-law cement grout, only considering the tortuosity of the rock and soil mass and only considering the time-varying property of the power-law cement grout are 0.1472 m, 0.1169 m and 0.1405 m respectively, and the experimental value carried out according to the implementation is 0.0978 m. At the same time, by analyzing FIG. 7, it can be seen that the theoretical value of the diffusion radius acquired by the method for determining the column-hemispherical permeation radius with the time-varying property of the power-law cement grout and the tortuosity of the rock and soil mass considering the coupling effect both the time-varying property of the power-law cement grout and the tortuosity of the rock and soil mass in the present embodiment is closer to the experimental value than the theoretical values of the diffusion radius respectively acquired by using the methods for calculating the column-hemispherical permeation grouting diffusion radius considering neither the tortuosity of the rock and soil mass nor the time-varying property of the power-law cement grout, only considering the tortuosity of the rock and soil mass and only considering the time-varying property of the power-law cement grout.

In summary, the method for determining the column-hemispherical permeation radius with the time-varying property of the power-law cement grout and the tortuosity of the rock and soil mass considering the coupling effect both the time-varying property of the power-law cement grout and the tortuosity of the rock and soil mass according to the disclosure can better reflect the permeation grouting diffusion law of the power-law cement grout in the rock and soil mass, and more accords with the grouting engineering practice, thereby provides theoretical guidance and technical reference for the practical grouting engineering design and construction of the rock and soil mass.

The above embodiments are only preferred embodiments of the disclosure, and do not limit the protective scope of the disclosure. All changes made by adopting the design principle of the disclosure and non-creative labor on this basis should fall within the protective scope of the disclosure.

What is claimed is:

1. A method for determining a column-hemispherical permeation radius, comprising:

acquiring a porosity $\phi$ of a rock and soil mass and a corresponding permeation coefficient K by geotechnical tests, and measuring a groundwater pressure $P_0$ at a grouting point and determining a tortuosity $\xi$ of the rock and soil mass;

acquiring an initial consistency coefficient $c_0$, a rheological index n and a time-varying property coefficient k of a power-law cement grout with a designed water to cement ratio by rheological tests, and determining a viscosity of the water $\mu_w$;

acquiring grouting parameters, the grouting parameters comprising a grouting pressure $P_1$, grouting time t, a number m of grouting holes of a side surface of a grouting pipe, and a grouting hole radius r; and solving a column-hemispherical permeation grouting diffusion radius R as the column-hemispherical permeation radius considering a coupling effect both the tortuosity of rock and soil mass and a time-varying property of the power-law cement grout by using a formula expressed as:

$$\Delta p = p_1 - p_0 = \frac{2^{1+n} c_0 e^{kt} \sqrt{\xi}}{1-2n} \left(\frac{m+1}{4m+5}\right)^n \left(\frac{3n+1}{tn}\right)^n \left(\frac{\phi \rho_w g}{8\mu_w K}\right)^{\frac{n+1}{2}} (R^{1-2n} - r^{1-2n}) R^{3n} \quad (1)$$

where $\rho_w$ represents a water density; g is gravitational acceleration; e represents a base of natural logarithm;

wherein an expression formula of the tortuosity $\xi$ of the rock and soil mass is:

$$\xi = \left(\frac{L_e}{L}\right)^2 \quad (3)$$

where $L_e$ represents an actual flow path length of the cement grout into the rock and soil mass; L is a linear length corresponding to the actual flow path of the cement grout into the rock and soil mass; and wherein an expression formula of the porosity $\phi$ of the rock and soil mass is:

$$\phi = 1 - \frac{\rho}{G_S \rho_W^{4°C}(1+\omega)} \quad (2)$$

where $\rho_W^{4°\,C.}$ is a density of pure distilled water at 4° C.; $\rho$ represents a density of the rock and soil mass; $\omega$ represents a mass water content of the rock and soil mass; $G_S$, represents a specific gravity of the rock and soil mass;

wherein the method further comprises: grouting the rock and soil mass with the power-law cement grout in a grouting engineering practice based on the column-hemispherical permeation radius obtained after the solving.

2. The method according to claim 1, wherein the density $\rho$ of the rock and soil mass is acquired by one of an irrigation method, a sand filling method, and a cutting ring method.

3. The method according to claim 1, wherein the mass water content $\omega$ of the rock and soil mass is measured by a drying method.

4. The method according to claim 1, wherein the specific gravity $G_S$ of the rock and soil mass is measured by combining a pycnometer method and a siphon cylinder method.

5. The method according to claim 1, wherein the permeation coefficient K is acquired by field water injection tests.

6. The method according to claim 1, wherein the acquiring an initial consistency coefficient $c_0$, a rheological index n and a time-varying property coefficient k of the power-law cement grout with a designed water to cement ratio by rheological tests comprises:

performing the rheological tests of the power-law cement grout with the designed water to cement ratio at different times by using a rotary viscometer or a capillary viscometer;

establishing a shear velocity-shear stress coordinate system, and acquiring rheological curves corresponding to the rheological tests;

obtaining a rheological equation corresponding to the rheological curve in accordance with a power-law fluid rheology equation, and then acquiring a consistency coefficient c and the rheological index n correspondingly; and obtaining the initial consistency coefficient $c_0$, the rheological index n and the time-varying property coefficient k of the power-law cement grout with the designed water to cement ratio by analyzing change relationships between the consistency coefficient c, the rheological index n and a time.

7. A method for determining a column-hemispherical permeation radius, comprising:

acquiring a porosity $\phi$ of a rock and soil mass and a corresponding permeation coefficient K by geotechnical tests, and measuring a groundwater pressure $P_0$ at a grouting point and determining a tortuosity $\xi$ of the rock and soil mass;

acquiring an initial consistency coefficient $c_0$, a rheological index n and a time-varying property coefficient k of a power-law cement grout with a designed water to cement ratio by rheological tests, and determining a viscosity of the water $\mu_w$;

acquiring grouting parameters, the grouting parameters comprising a grouting pressure $P_1$, grouting time t, a number m of grouting holes of a side surface of a grouting pipe, and a grouting hole radius r;

solving a column-hemispherical permeation grouting diffusion radius R as the column-hemispherical permeation radius considering a coupling effect both the tortuosity of rock and soil mass and a time-varying property of the power-law cement grout by using a formula expressed as:

$$\Delta p = p_1 - p_0 = \frac{2^{1+n} c_0 e^{kt} \sqrt{\xi}}{1-2n}\left(\frac{m+1}{4m+5}\right)^n \left(\frac{3n+1}{tn}\right)^n \left(\frac{\phi \rho_w g}{8\mu_w K}\right)^{\frac{n+1}{2}} (R^{1-2n} - r^{1-2n})R^{3n}$$

where $\rho_w$ represents a water density; g is gravitational acceleration; e represents a base of natural logarithm;

wherein an expression formula of the tortuosity $\xi$ of the rock and soil mass is:

$$\xi = \left(\frac{L_e}{L}\right)^2$$

where $L_e$ represents an actual flow path length of the cement grout into the rock and soil mass; L is a linear length corresponding to the actual flow path of the cement grout into the rock and soil mass; and wherein an expression formula of the porosity $\phi$ of the rock and soil mass is:

$$\phi = 1 - \frac{\rho}{G_S \rho_W^{4°C}(1+\omega)}$$

where $\rho_W^{4°\,C.}$ is a density of pure distilled water at 4° C.; $\rho$ represents a density of the rock and soil mass; $\omega$ represents a mass water content of the rock and soil mass; $G_S$ represents a specific gravity of the rock and soil mass; and applying the column-hemispherical permeation radius as a reference in practical grouting engineering of the power-law cement grout into the rock and soil mass.

* * * * *